United States Patent
Wang et al.

(10) Patent No.: US 8,747,728 B2
(45) Date of Patent: Jun. 10, 2014

(54) METHOD AND SYSTEM FOR MANUFACTURING A POLYMER ENDOPROSTHESIS BY INJECTION MOLDING AND BLOW MOLDING

(75) Inventors: Yunbing Wang, Sunnyvale, CA (US); James Oberhauser, Saratoga, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 238 days.

(21) Appl. No.: 13/114,941

(22) Filed: May 24, 2011

(65) Prior Publication Data

US 2012/0299226 A1 Nov. 29, 2012

(51) Int. Cl.
*B29C 49/06* (2006.01)

(52) U.S. Cl.
USPC ............................................ 264/537; 264/532

(58) Field of Classification Search
None
See application file for complete search history.

(56) References Cited

U.S. PATENT DOCUMENTS

| | | | |
|---|---|---|---|
| 3,002,225 A | | 10/1961 | Goller |
| 4,155,974 A | * | 5/1979 | Valyi ............................ 264/513 |
| 7,476,245 B2 | | 1/2009 | Abbate |
| 7,622,070 B2 | | 11/2009 | Atladottir et al. |
| 8,043,553 B1 | * | 10/2011 | Durcan ......................... 264/573 |
| 2006/0020330 A1 | | 1/2006 | Huang et al. |
| 2008/0001330 A1 | | 1/2008 | Huang et al. |
| 2008/0275537 A1 | | 11/2008 | Limon |
| 2009/0001633 A1 | | 1/2009 | Limon et al. |
| 2011/0066222 A1 | | 3/2011 | Wang et al. |

FOREIGN PATENT DOCUMENTS

| | | |
|---|---|---|
| DE | 21 43 262 | 3/1973 |
| FR | 76 005 | 9/1961 |
| GB | 692 590 | 6/1953 |
| WO | WO 2008/002636 | 1/2008 |
| WO | WO 2008/090324 | 7/2008 |

OTHER PUBLICATIONS

"Polylactic acid" Wikipedia, downloaded from www.en.wikipedia.org/wiki/Polylactic_acid, 5 pgs. Sep. 24, 2012.
International Search Report and Written Opinion for PCT/US2012/039164, mailed Oct. 9, 2012, 17 pgs.

* cited by examiner

*Primary Examiner* — Monica Huson
(74) *Attorney, Agent, or Firm* — Squire Sanders (US) LLP (57) ABSTRACT

A polymer endoprosthesis is fabricated by a combination of injection molding and blow molding which form a tubular substrate of polymer material, followed by laser cutting, crimping and sterilization. After the injection and blow molding processes, a subtractive process is performed on the tubular substrate to transform it into a stent having a network of stent struts. The tubular substrate can be made in an injection mold and blow mold which are attached to each other. The transition from injection molding and blow molding can be performed while the injection molded substrate remains at a temperature at or above Tg of the polymer material.

20 Claims, 5 Drawing Sheets

METHOD AND SYSTEM FOR MANUFACTURING A POLYMER ENDOPROSTHESIS BY INJECTION MOLDING AND BLOW MOLDING

FIELD OF THE INVENTION

This invention relates generally to fabrication of implantable endoprostheses, more particularly, to fabrication of polymer stents from injection molded and blow molded tubes.

BACKGROUND OF THE INVENTION

An endoprosthesis is an artificial device that is placed inside a human or animal body. An anatomical lumen is a cavity of a tubular organ such as a blood vessel. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. In such treatments, stents reinforce blood vessels and prevent restenosis following angioplasty in the vascular system.

Stents are relatively small, as they are often required to be passed through tight confines of anatomical lumens. A stent must often have great longitudinal flexibility to allow it to pass through tortuous curves of anatomical lumens. Stents typically comprise a fine network of struts which form a tubular scaffold. The tubular scaffold must often be capable of being crimped onto a delivery device, such as a balloon, to reduce its size to allow passage through anatomical lumens, and then forcibly expanded by the balloon to an enlarged, deployed state at the desired location within the body. For some stents, the tubular scaffold must be capable of self-expanding from its crimped state at the desired location within the body. After implantation and deployment, the tubular scaffold must have sufficient strength to support surrounding anatomical structures. Thus it will be appreciated that stents present unique design challenges.

Stents have in the past been made of metals, such as nickel-titanium alloys having shape memory and superelastic properties. The advent of polymer stents have presented further design challenges. The design of a polymer stent must take into account that, as compared to metal stents of the same dimensions, polymer stents typically have less radial strength and rigidity and less fracture toughness. Thus, there is a continuing need for a method and system for manufacturing polymer stents that (a) increase uniformity from stent to stent, (b) allow for tight control of design parameters, such as the thickness and dimension of individual stent struts, and/or (c) increase manufacturing efficiency.

SUMMARY OF THE INVENTION

Briefly and in general terms, the present invention is directed to a method and system for forming a polymer endoprosthesis.

In aspects of the present invention, a method comprises injecting a polymer material into a cavity of a first mold in order to form a stock tube, placing the stock tube in a cavity of a second mold, wherein the stock tube enters the second mold as it exits the first mold, and expanding the stock tube to form a precursor tube within the second mold.

In aspects of the present invention, a method comprises forming a stock tube of polymer material in an injection mold, transferring the stock tube from the injection mold to a blow mold, the transferring step performed while the stock tube is at a temperature at or above Tg of the polymer material, and expanding the stock tube in the blow mold in order to form a precursor tube.

In aspects of the present invention, a system comprises an injection mold having an injection mold cavity, a blow mold having a blow mold cavity, and a door movable from an first position to a second position, the injection mold cavity and the blow mold cavity being separated from each other by the door when at the first position, the injection mold cavity and the blow mold cavity being exposed to each other with when the door is at the second position.

The features and advantages of the invention will be more readily understood from the following detailed description which should be read in conjunction with the accompanying drawings.

DETAILED DESCRIPTION OF PREFERRED EMBODIMENTS

All publications and patents mentioned in the present specification are incorporated herein by reference to the same extent as if each individual publication or patent was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. For example without limitation, a material that is described as "substantially at ambient room temperature" refers to a material that is perfectly stabilized at room temperature and a material that one skilled in the art would readily recognize as being at room temperature even though some areas of the material are not perfectly at room temperature. In general, but with the preceding discussion in mind, a numerical value herein that is modified by a word of approximation may vary from the stated value by ±15%, unless expressly stated otherwise.

Figure 1:
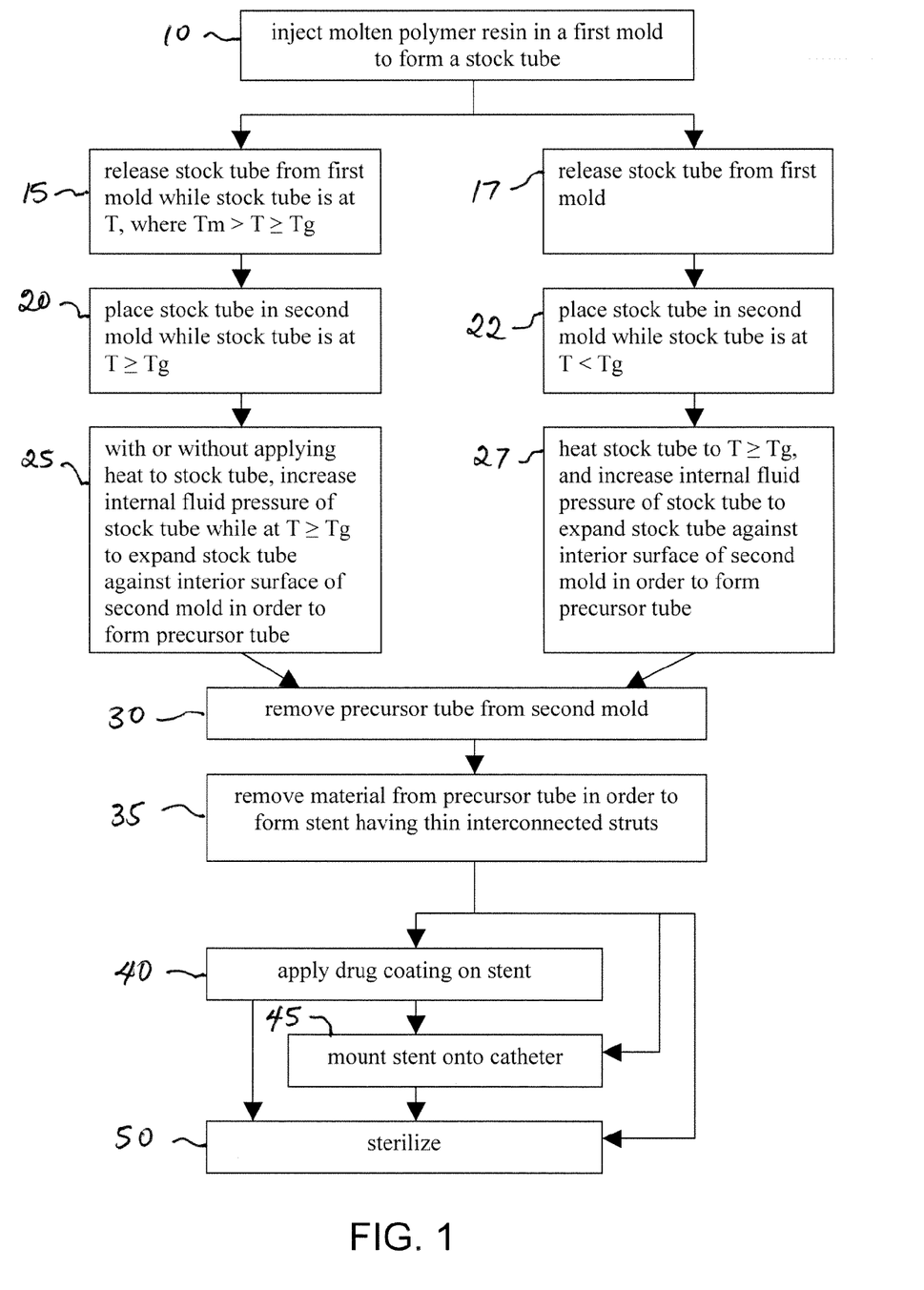
FIG. 1 is flow diagram showing a method according to some embodiments of the present invention.

Referring now in more detail to the exemplary drawings for purposes of illustrating embodiments of the invention, wherein like reference numerals designate corresponding or like elements among the several views, there is shown in FIG. 1 a flow diagram of a method for manufacturing a polymer endoprosthesis which involves a combination of injection molding, blow molding, and formation of stent struts. Injection molding is performed first and is followed by deformation of the injection molded item, then forming the network or pattern of stent struts from the deformed injection molded item.

Methods of injection molding a polymer stent have been described in, for example, U.S. Pub. No. 2008/0001330 of application Ser. No. 11/477,333 filed Jun. 28, 2006. In prior methods, the network of stent struts was formed during the injection molding process. A potential difficulty in having stent struts formed directly through injection molding is that the mold cavity will have grooves that correspond to the intricate shapes and pattern of the desired stent struts. The polymer resin would have to flow through the network of grooves that can be 0.1 mm wide and 0.1 mm deep, or even smaller. Depending on the actual width and depth of the grooves, the viscosity of the molten resin, and manufacturing throughput requirements, it may be impractical to have stent struts formed directly from injection molding.

In some embodiments of present invention, none of the stent struts in the finished stent are formed through injection molding. In alternative embodiments, some stent struts are formed through injection molding (an additive process) and other stent struts on the same stent are formed at a later time by removal of material (a subtractive process) as described below.

Prior to formation of the stent struts by a subtractive process, changes are made to the mechanical characteristics of the injection molded item from which the stent struts will later be formed. The structure from which stent struts are formed, such as the injection molded item of the present invention, is referred to herein as the "substrate." In general, a substrate can be a flat sheet or a cylindrical tube. After injection molding, the mechanical characteristics of the substrate can be changed by inducing deformation, such as by stretching, in one or more directions. Such deformation causes polymer molecule chains to become oriented in a particular direction and/or causes polymer crystallization and growth in a particular direction. These morphological changes involving microstructure orientation give the substrate the desired mechanical characteristics which will allow a network of stent struts, subsequently formed from the substrate, to have the necessary balance between flexibility, strength, and fracture toughness.

Methods of deforming the injection molded substrate can involve blow molding. For a description of blow molding, see, for example, U.S. Pub. No. 2009/0001633 of application Ser. No. 11/771,967 filed Jun. 29, 2007 and U.S. Pub. No. 2011/0066222 of application Ser. No. 12/558,105 filed Jun. 28, 2006.

Referring again to FIG. 1, in block 10 polymer material is heated until it is molten, then injected under pressure into the cavity of a first mold. The cavity of the first mold is annular in shape. The first mold is configured to form a tube of the polymer, which is a substrate from which stent struts will be formed at a later time. At this stage (prior to making morphological changes to the substrate), the substrate is referred to as a "stock tube." The shape and dimensions of the stock tube corresponds to those of the annular mold cavity. The stock tube is cylindrical and has a circumferential wall having a predetermined wall thickness. The wall thickness is carefully selected to provide optimal results in the finished stent. The wall thickness can be, without limitation, about 1 mm. The thickness can be selected based in part on the polymer material being used and the amount of expansion the substrate will be subjected to at a later time. Optionally, the circumferential wall has no radial perforations though there can be axial openings at the opposite ends of the circumferential wall.

In some embodiments, the method proceeds to block 15 in which the stock tube is released from the first mold while still at a temperature greater than the glass temperature (Tg) of the polymer material but lower than the melt temperature (Tm) of the polymer material. Tg is the temperature at which the amorphous domains of a polymer change from a brittle vitreous state to a solid deformable or ductile state at atmospheric pressure. Tg corresponds to the temperature where the onset of segmental motion in the chains of the polymer occurs. Between Tg and Tm rotational barriers exist, however, the barriers are not great enough to substantially prevent segmental mobility.

The polymer material is at a temperature substantially below Tm when released from the first mold. It is to be understood that the stock tube is in a substantially non-molten state when it comes out of the first mold, even though it is at a temperature at or above Tg. Having the stock tube substantially non-molten helps to ensure that the circumferential wall thickness is not inadvertently altered in the time period between release from the first mold (block 15) and expansion in the second mold (block 25 discussed below). This non-molten state of the stock tube upon release from the first mold is distinct from extrusion processes in which an extruded polymer is substantially molten when it exits an extruder die.

The stock tube is released from the first mold after the flow of polymer material in the mold cavity has substantially stopped. This condition is distinct from extrusion processes in which the polymer material continues to flow through the extruder cavity while exiting the extruder die.

Next in block 20, before the stock tube has cooled to a temperature substantially below Tg, the stock tube is placed in the cavity of a second mold, which can be a glass-lined blow mold. The cavity has an inner diameter that is greater than the outer diameter of the stock tube.

In some embodiments of the present invention, at least some portions of the first mold are contained within the cavity of the second mold. Upon completion of polymer material injection, those portions of the first mold can open and thereby eject or release the stock tube directly from the first mold cavity and into the cavity of the second mold. This direct transfer of the stock tube from the first mold to the second mold, without exposure to external atmospheric conditions and handling, eliminates or minimizes cooling of the stock tube and eliminates or minimizes the chance of inadvertent alteration of the circumferential wall thickness prior to expansion in the second mold (block 25 discussed below).

Next in block 25, the internal fluid pressure of the stock tube is increased, such as by pumping a gas into the stock tube. The internal fluid pressure is increased to a level which causes the circumferential wall of the stock tube (i.e., substrate) to stretch and expand radially outward against the surfaces of the second mold cavity, thereby changing the mechanical characteristics of the substrate. The surfaces of the second mold cavity limit the outward radial expansion of the circumferential wall.

Upon completion of block 25, after changes to the mechanical characteristics of the substrate have been made, the substrate is referred to as a "precursor tube."

In some embodiments, substantially the entire longitudinal length of the stock tube is radially expanded simultaneously. In alternative embodiments, expansion of the stock tube occurs in a progressive manner, as described in Pub. No. 2011/0066222, in which a limited longitudinal segment of the stock tube is radially expanded at any one time, and the deformation propagates longitudinally over a period of time from one end of the stock tube to the other end.

By keeping the substrate at a temperature above Tg during transfer from the first mold to the second mold, manufacturing time is decreased by eliminating or reducing the need to reheat the substrate to a temperature necessary for expansion. In some embodiments, the substrate has not cooled to a temperature below a predetermined process temperature (Tp) prior to expansion of the substrate, thereby allowing expansion to be performed substantially without applying heat to the substrate. The process temperature is carefully predetermined to provide optimal results in the finished stent. Typically, Tp is between Tg and Tm. Tp can depend in part on the composition of the polymer material and the desired amount of radial expansion. For example, Tp can be from about 160 degrees F. to about 220 degrees F. when the polymer material being used is poly(L-lactide). Without limitation, the composition of the polymer material, levels for Tp, internal fluid pressure, radial expansion ratio, axial extension ratio, and other blow molding parameters can be as described in U.S. Pub. No. 2011/0066222 of application Ser. No. 12/558,105 filed Jun. 28, 2006.

In some embodiments, the substrate is heated during or before expansion of the circumferential wall, even though the substrate has not cooled to a temperature below Tg subsequent to removal from the first mold. The application of heat in block 20 and/or block 25 can help ensure uniformity in temperature and uniformity in the resultant mechanical characteristics. The application of heat may be needed to bring the stock tube to a temperature at or about Tp.

Next in block 30, the precursor tube is removed from the second mold. In some embodiments, the precursor tube which is removed from the second mold is used as an endoprosthesis.

Continuing from block 30 to block 40, material is removed from the precursor tube, in what is referred to as a subtractive process, in order to form a stent having a network of stent struts. Material is removed from the precursor tube so that what remains of the precursor tube is the network of stent struts. Material can be removed with a cutter, which can be sharp blade and/or a laser cutting tool. For a description of laser removal from a polymer substrate, see, for example, U.S. Pat. No. 7,622,070 issued Nov. 24, 2009.

Next in block 50, the stent is sterilized, making it ready for implantation within a patient. Sterilization can be performed in any number of ways, such as by ethylene oxide gas or electron beam (E-beam) radiation.

Alternatively, as shown in block 45, the stent can be mounted onto a catheter prior to sterilization. Mounting can involve crimping the stent onto an inflatable balloon of the catheter.

Alternatively, as shown in block 40, a coating can be applied to the stent prior to sterilization or prior to mounting the stent onto a catheter. The composition of the coating and any drugs carried therein can be as described in any of the publications which are cited and incorporated herein by reference.

In alternative embodiments of the present invention, the method can proceed from block 10 to block 17 in which the stock tube is released from the first mold at any temperature. For example, the stock tube can be removed from the first mold after the polymer material in the injection mold cavity has cooled to a temperature T, where T<Tg or where Tg<T<Tm.

Continuing from block 17 to block 22, the stock tube is placed in the cavity of a second mold. The cavity has an inner diameter that is greater than the outer diameter of the stock tube. This step can be performed after the stock tube is at a temperature about the same as ambient room temperature, such as in situations where the stock tube has been stored for a long period of time prior to placement in the second mold. Alternatively, this step (placing the stock tube in the second mold) can be performed while the stock tube is still at a temperature substantially above room ambient temperature due to heat from injection molding. Alternatively, this step (placing the stock tube in the second mold) can be performed while the stock tube is at a temperature substantially below ambient room temperature, such as in situations where the stock tube has been actively cooled or quenched within the first mold or upon removal from the first mold.

Next in block 27, the internal fluid pressure of the stock tube (i.e., substrate) is increased, such as by pumping a gas into the stock tube, in order to cause expansion and produce the precursor tube. Expansion is the result of a pressure differential in which fluid pressure outside of the stock tube is lower than pressure inside the stock tube. While the substrate is in the second mold, the substrate is heated to a process temperature (Tp) above Tg and below Tm. Parameters such as internal fluid pressure, Tp, and others can be as previously described in connection with block 25.

The method proceeds from block 27 to blocks 30-50 previously described with optional application of a drug coating and optional mounting onto a catheter.

As indicated above, the method can include a series of steps with blocks 15, 20 and 25, or alternatively, a series of steps with blocks 17, 22 and 27. The method with blocks 15, and 25 is optionally performed as described below in connection with FIGS. 2A-2F. The method with blocks 17, 22 and 27 is optionally performed as described below in connection with FIGS. 3A-3F. It is to be understood that the method described above in connection with blocks 10-50 can be performed using systems other than those shown in FIGS. 2A-3F.

FIGS. 2A-2F show a system for manufacturing a polymer endoprosthesis, with each figure illustrating a sequential step.

Figure 2A:
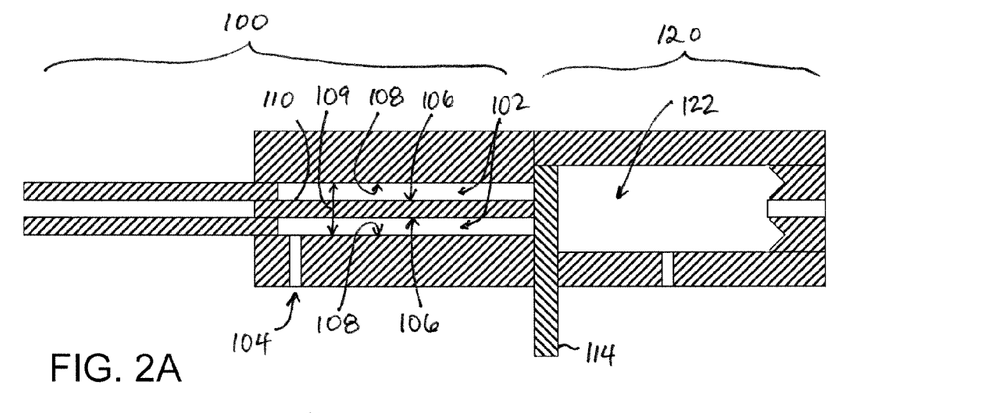
FIG. 2A is a cross-section view of a system according to some embodiments of the present invention, showing the system prior to injection of a polymer resin.
Figure 2B:
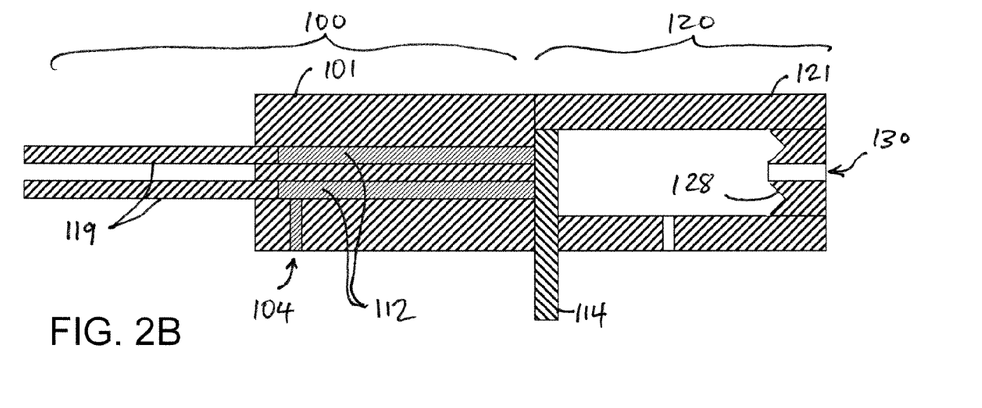
FIG. 2B is a cross-section view of the system of FIG. 2A, showing the system after polymer resin is injected into an injection mold cavity.

An injection molding process is shown in FIGS. 2A and 2B. Injection mold 100 includes cavity 102 into which molten polymer resin is injected through gate 104. The cavity is configured to produce a stock tube. The cavity is cylindrical in shape and is bounded by inner circumferential surface 106 and outer circumferential surface 108 of mold 100. The distance between circumferential surfaces 106 and 108 defines the thickness of the circumferential wall of the resultant stock tube. Outer circumferential surface 108 defines a maximum diameter 109 of injection mold cavity 102. The size and shape of the exterior surface of the resultant stock tube will correspond to the outer circumferential surface 108. Inner circumferential surface 106 is provided by mold core 110 in the shape of a cylindrical rod. The size and shape of the interior lumen of the resultant stock tube will be that of mold core 110.

FIG. 2B shows polymer resin 112 having been injected through injection gate 104 and into injection mold cavity 102. It is to be understood that there can be one or more injection gates and that the injection gates can be arrange and oriented in any suitable manner, such as to prevent voids and other structural defects in the resultant stock tube. When the flow of polymer resin 112 into injection mold cavity 102 has stopped and after polymer resin 112 has cooled to a temperature below Tm, door 114 slides from a closed position shown in FIG. 2B to an open position shown in FIG. 2C. Door 114 can be pneumatically or electrically controlled.

Figure 2C:
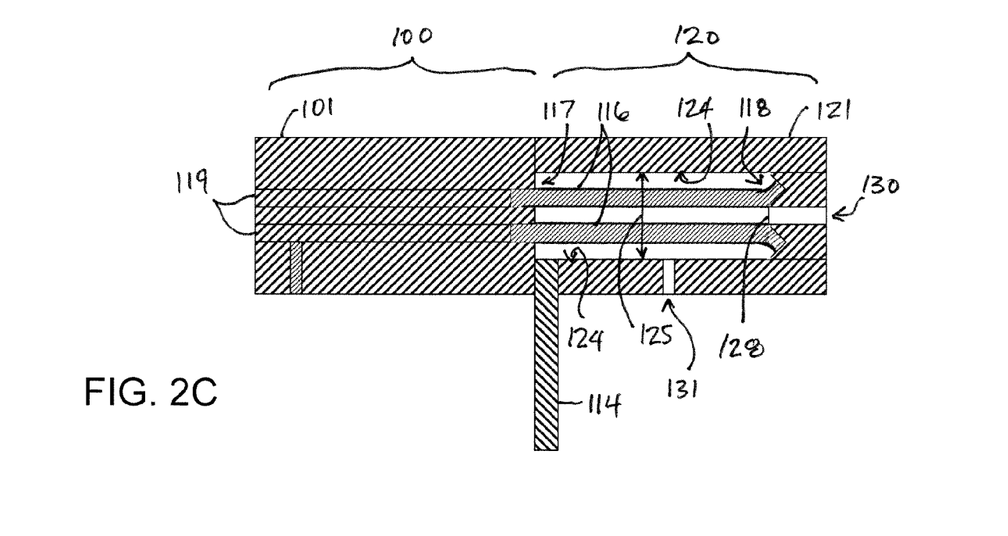
FIG. 2C is a cross-section view of the system of FIG. 2A, showing the system after the polymer resin, referred to as a stock tube, is ejected in a non-molten state directly into a blow mold cavity.

As shown in FIG. 2C, movement of door 114 allows the non-molten polymer resin, referred to now as stock tube 116, to be released from injection mold 100 and placed into blow mold 120. Injection mold 100 and blow mold 120 are connected to each other such that movement of door 114 exposes stock tube 116 to cavity 122 of blow mold 120. With door 114 at its open position, injection mold cavity 102 and blow mold cavity 122 form a common, enlarged cavity that is substantially sealed from the external, ambient environment by the interconnected housings 101 and 121 of injection mold 100 and blow mold 120. With door 114 open, injection mold cavity 102 and blow mold cavity 122 are exposed to each other. After door 114 has opened, ejector 119 pushes stock tube 116 out of injection mold cavity 102 and directly into blow mold cavity 122. Ejector 119 can be pneumatically or electrically controlled. Stock tube 116 is transferred from injection mold cavity 102 into blow mold cavity 122 while shielded from the external, ambient environment.

Blow mold cavity 122 is bounded by circumferential surface 124 which defines a maximum diameter 125 of the blow mold cavity 122. Diameter 125 is greater than maximum diameter 109 of injection mold cavity 102, which thus allows space for stock tube 116 to expand radially outward.

There are axial openings at opposite end segments 117 and 118 of stock tube 116. First end segment 117 remains partially contained within injection mold 100 so that the axial opening at first end segment 117 is sealed against fluid flow. Second end segment 118 is engaged against conical member 128 of blow mold 120. Conical member 128 is wedged into second end 118 to prevent fluid flow through the interface between second end 118 and conical member 128. Gas passageway 130 extends through the center of conical member 118 and is in communication with the interior of stock tube 116.

Figure 2D:
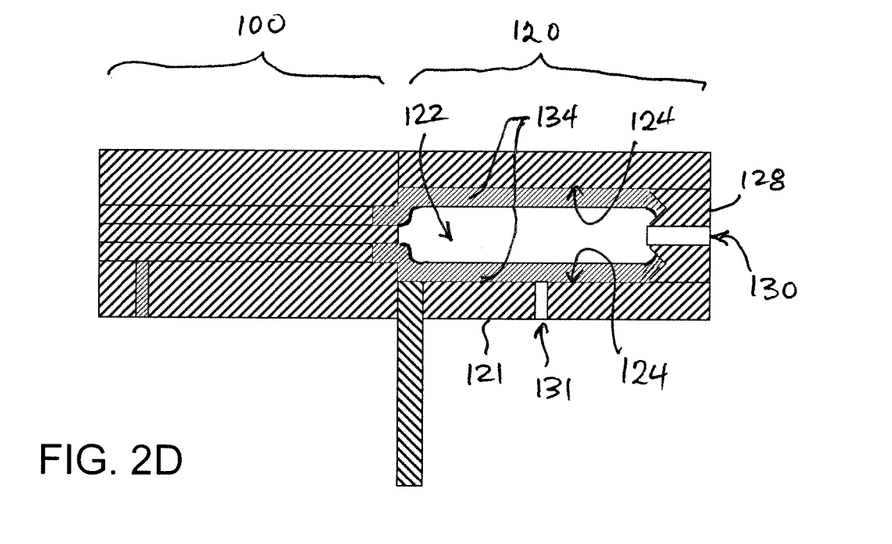
FIG. 2D is a cross-section view of the system of FIG. 2A, showing the system after the stock tube is radially expanded against an interior surface of the blow mold cavity.

FIG. 2D shows the result after gas is pumped through gas passageway 130 and into the interior of stock tube 116. The gas has increased the fluid pressure within the interior of stock tube 116 to a level which caused the circumferential wall of stock tube 116 to expand radially outward and press against circumferential surface 124 of blow mold cavity 122. Blow mold 120 can include vent 131 in its housing 121 to allow gas between the circumferential wall of stock tube 116 and circumferential surface 124 of blow mold cavity 122 to escape during expansion of the circumferential wall. After expansion is completed, blow mold 120 can be opened to allow for removal of the expanded stock tube, now referred to as precursor tube 134. For example, conical member 128 can be retracted out of blow mold 120 to provide an opening through which precursor tube 134 can pushed by ejector 119 of injection mold 100.

Figure 2E:
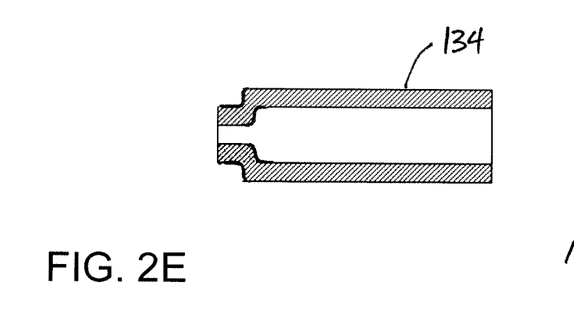
FIG. 2E is a cross-section view of the expanded polymer resin, referred to as a precursor tube, after having been removed from the blow mold.

FIG. 2E shows precursor tube 134 after having been removed from blow mold 120.

Figure 2F:
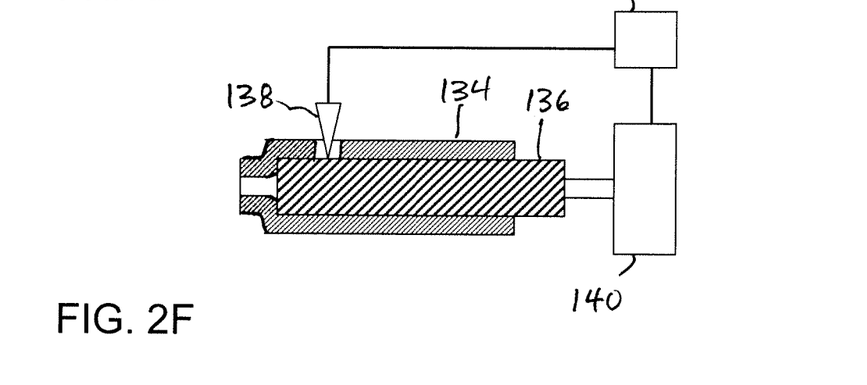
FIG. 2F is a cross-section view of the precursor tube carried on a mandrel, showing a cutter removing material from the precursor tube in order form stent struts.

As shown in FIG. 2F, precursor tube 134 can be carried on cylindrical mandrel 136 and placed adjacent cutter 138 for removing portions of precursor tube 134 to form a network of stent struts. Perforation 139 has been made by cutter 138 through precursor tube 134. With removal of material, precursor tube 134 is transformed to a stent having a network of stent struts. Mandrel 136 is inserted within precursor tube 134 and can be connected to rotation and slide motor and gear assembly 40 under computer numerical control (CNC). Relative movement between mandrel 136 and cutter 138 can be programmed into a CNC software application operating within electronic controller 142 to provide the desired pattern of stent struts.

FIGS. 3A-3F show a system for manufacturing a polymer endoprosthesis, with each figure illustrating a sequential step.

Figure 3A:
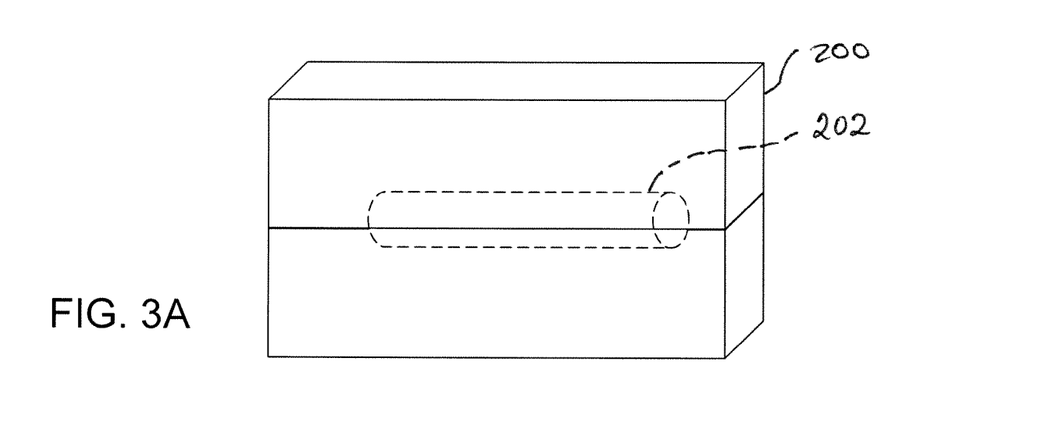
FIGS. 3A-3F are perspective views of a system according to some embodiments of the present invention, showing a stock tube formed from polymer resin injected into an injection mold, and showing a precursor tube formed from the stock tube having been expanded in a blow mold, and showing a stent being formed by removal of material from the precursor tube.
Figure 3B:
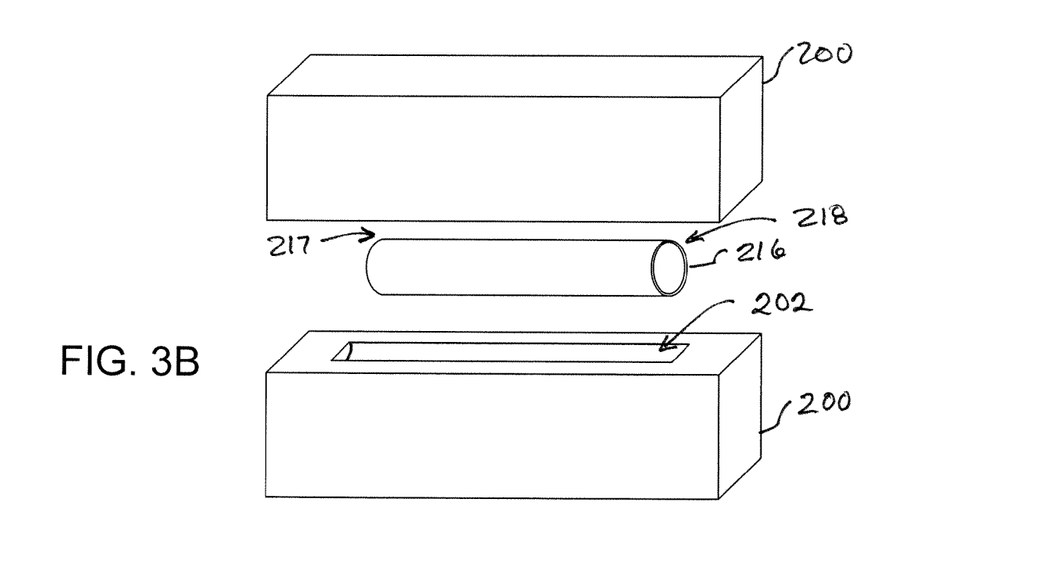

An injection molding process is shown in FIGS. 3A and 3B. Injection mold 200 includes cavity 202 into which molten polymer resin is injected. Mold cavity 202 is configured to produce stock tube 116 having a circumferential wall with a predetermined wall thickness.

FIG. 3B shows two halves of injection mold 200 separated to expose mold cavity 202 and allow stock tube 116 to be ejected out from mold cavity 202. Prior to ejection, a mold core can retracted out from the interior of stock tube 116. There are axial openings at opposite end segments 117, 118 of stock tube 116. In some embodiments, stock tube 116 has only one axial opening in which end segment 117 is closed and end segment 118 is open to allow for introduction of gas during blow molding.

Stock tube 116 is in a substantially non-molten state when it is ejected from injection mold 220. In some embodiments, stock tube 116 is at a temperature between Tg and Tm when ejected from injection mold 220. In alternative embodiments, stock tube 116 is at a temperature below Tg when ejected from injection mold 220.

The injection molded item, namely stock tube 216, has no pattern of stent struts and no radial perforations distributed across the longitudinal length of the stent.

Figure 3C:
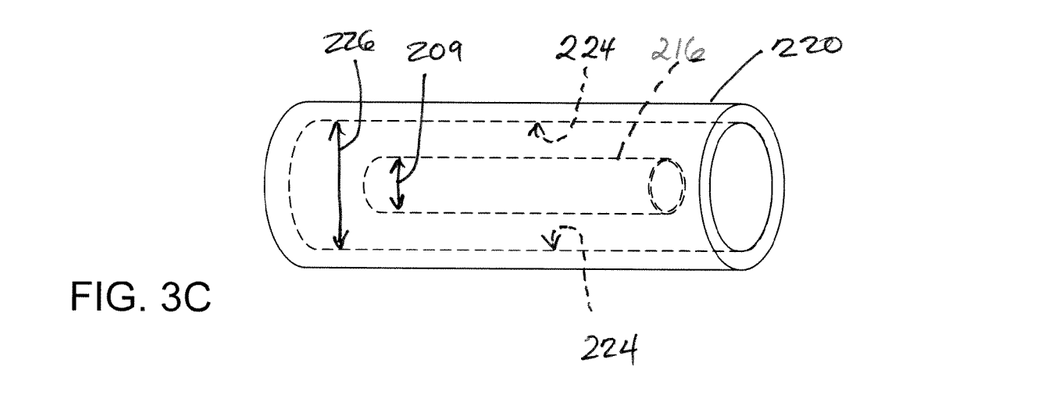

Next, as shown in FIG. 3C, stock tube 116 is place within blow mold 220. The step of transferring stock tube 116 from injection mold 200 to blow mold 220 can be done before stock tube 116 is able to cool to a temperature that is either: (a) below a desired process temperature (Tp) predetermined to produce optimal results in the finished stent, where Tg<Tp<Tm; or (b) below Tg of the polymer resin. For example, stock tube 116 can be actively cooled or quenched within injection mold 200 or upon removal from injection mold 200.

Blow mold 220 has an interior diameter 226 which is greater than the maximum outer diameter 209 of the circumferential wall of stock tube 116 to allow for radial expansion of the circumferential wall. Interior surface 224 of blow mold 220 limits radial expansion of the circumferential wall. Optionally, blow molding including the application of heat is performed as described in U.S. Pub. Nos. 2009/0001633 and/or 2011/0066222.

Figure 3D:
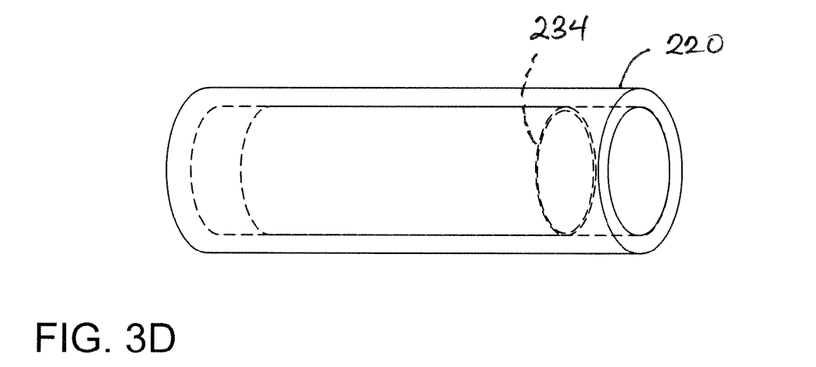

FIG. 3D shows the result after gas is pumped into the interior of stock tube 216. At this stage, the expanded stock tube is referred to as precursor tube 234.

Figure 3E:
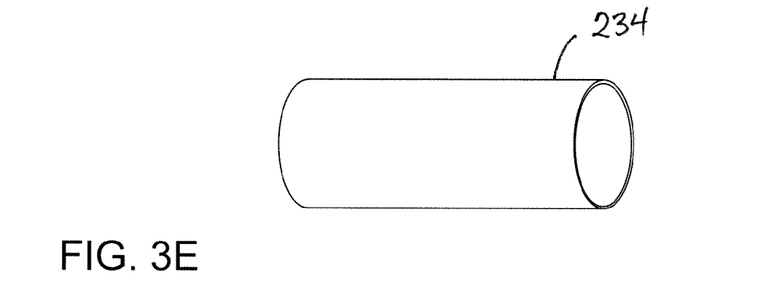

FIG. 3E shows precursor tube 234 after having been removed from blow mold 220.

Figure 3F:
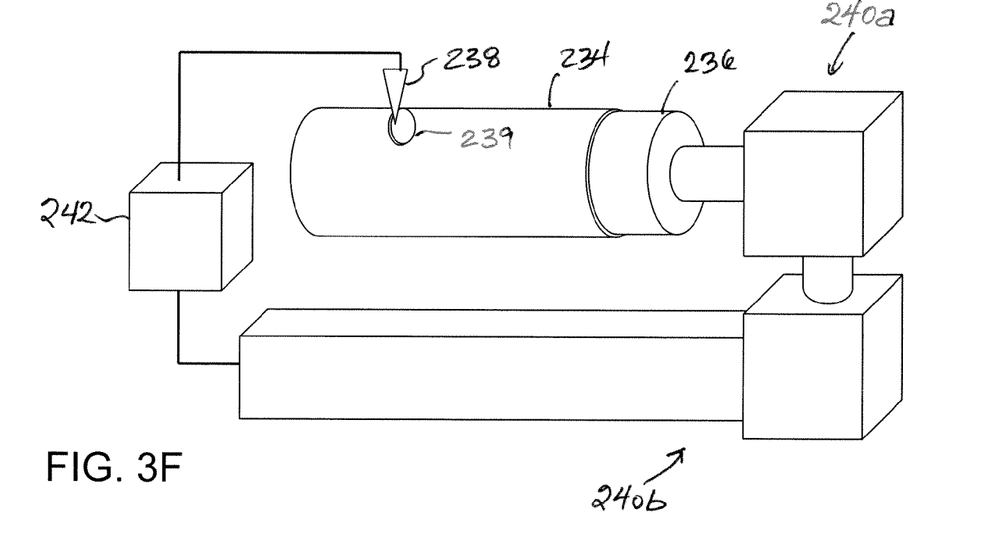

As shown in FIG. 3F, precursor tube 234 can be carried on cylindrical mandrel 236 and placed adjacent cutter 238 for removing portions of precursor tube 234 to form a network of stent struts. Perforation 239 has been made by cutter 238 through precursor tube 234. With removal of material, precursor tube 234 is transformed to a stent having a network of stent struts. Mandrel 236 is inserted within precursor tube 234 and can be connected to rotation motor and gear assembly 240a and slide motor and gear assembly 240b under computer numerical control (CNC). Relative movement between mandrel 236 and cutter 238 can be programmed into a CNC software application operating within electronic controller 242 to provide the desired pattern of stent struts.

In the above-described system and method, the polymer material or resin can be any synthetic or naturally occurring polymer suitable for implantation. Without limitation, the material can be selected from the group consisting of poly(L-lactide) ("PLLA"), poly(L-lactide-co-glycolide) ("PLGA"), poly(L-lactide-co-D-lactide) ("PLLA-co-PDLA") with less than 10% D-lactide, and PLLD/PDLA stereocomplex, and PLLA-based polyester block copolymer containing a rigid segment and a soft segment, the rigid segment being PLLA or PLGA, the soft segment being PCL or PTMC.

In the above-described system and method, material is removed from the precursor tube to transform the precursor tube to a stent having stent struts arranged in any pattern. The stent struts can have the patterns described in U.S. Pub. No. 2008/0275537 of application Ser. No. 12/114,608 filed May 2, 2008 and U.S. Pat. No. 7,476,245 issued Jan. 13, 2009. For example, the pattern can include stent struts arranged in a repeating pattern of W-shaped cells as described in Pub. No. 2008/0275537 or in a repeating pattern of hour-glass shaped cells as described in U.S. Pat. No. 7,476,245. The shape of the cells can correspond to perforations 139 and 239 in FIGS. 2F and 3F. The pattern can include a series of longitudinally arranged rings, each ring having an undulating series of stent struts oriented at oblique angles to each other, and each one of the rings is connected to an adjacent ring by other stent struts oriented substantially parallel to the longitudinal axis of the stent. The present invention is not limited to any particular pattern.

In the above-described system and method, the first mold or the injection mold can have an annular mold cavity having inner diameter ID and outer diameter OD and the second mold or the blow mold can have a cylindrical mold cavity having a diameter D. The amount of radial expansion which the stock tube undergoes depends upon the dimensional relationship between the two mold cavities. Without limitation, the following approximate dimensions for ID, OD, and D can be used.

EXAMPLE 1

ID=about 0.17 mm; OD=about 0.41 mm; D=about 3.5 mm

EXAMPLE 2

ID=about 0.13 mm; OD=about 0.40 mm; D=about 3 mm

EXAMPLE 3

ID=about 0.11 mm; OD=about 0.34 mm; D=about 2.5 mm

The dimensions of the two mold cavities can be such that the circumferential wall of the substrate undergoes a radial expansion (RE) ratio in the range of about 300% to about 400%. RE ratio is defined as (Inside Diameter of Precursor Tube)/(Inside Diameter of Stock Tube). RE ratio as a percentage is defined as (RE ratio−1)×100%.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of forming a polymer endoprosthesis, the method comprising:
   injecting a polymer material into a cavity of a first mold in order to form a stock tube;
   placing the stock tube in a cavity of a second mold, wherein the stock tube enters the second mold directly from the first mold; and
   expanding the stock tube to form a precursor tube within the second mold.

2. A method of forming a polymer endoprosthesis, the method comprising:
   injecting a polymer material into a cavity of a first mold in order to form a stock tube;
   placing the stock tube in a cavity of a second mold, wherein the stock tube enters the second mold as it exits the first mold; and
   expanding the stock tube to form a precursor tube within the second mold;
   further comprising, after the injecting step and before the placing step, moving a door, which separates the cavity of the first mold from the cavity of the second mold, to an open position to expose the stock tube to the cavity of the second mold.

3. The method of claim 1, wherein the stock tube exits the first mold and enters the second mold before the stock tube has cooled to a temperature below Tg of the polymer material.

4. The method of claim 1, further comprising transforming the precursor tube into a stent having a network of stent struts.

5. The method of claim 4, wherein the transforming step includes making a plurality of perforations through a circumferential wall of the precursor tube.

6. The method of claim 2, wherein the stock tube exits the first mold and enters the second mold while at a temperature at or above Tg of the polymer material.

7. The method of claim 2, wherein the expanding step includes radially expanding the stock tube by introducing gas into the stock tube.

8. The method of claim 7, wherein the expanding step includes axially extending the stock tube.

9. The method of claim 2, further comprising transforming the precursor tube into a stent having a network of stent struts.

10. The method of claim 9, wherein the transforming step includes making a plurality of perforations through a circumferential wall of the precursor tube.

11. A method of forming a polymer endoprosthesis, the method comprising:
   forming a stock tube of polymer material in an injection mold;
   transferring the stock tube from the injection mold to a blow mold; and
   expanding the stock tube in the blow mold in order to form a precursor tube,
   wherein the stock tube has a temperature (T) and the transferring includes:
      releasing the stock tube from the injection mold while Tm>T≥Tg, wherein Tm is the melting temperature of the polymer material and Tg is the glass temperature of the polymer material, and followed by
      before T drops below Tg after the stock tube is released from the injection mold, placing the stock tube into a blow mold while T≥Tg.

12. The method of claim 11, wherein the expanding of the stock tube is performed without heating the stock tube after the stock tube is released from the injection mold.

13. The method of claim 11, further comprising transforming the precursor tube into a stent having a network of stent struts.

14. The method of claim 13, wherein the transforming step includes making a plurality of perforations through a circumferential wall of the precursor tube.

15. A method of forming a polymer endoprosthesis, the method comprising:
   forming a stock tube of polymer material in an injection mold;
   transferring the stock tube from the injection mold to a blow mold, the transferring step performed while the stock tube is at a temperature at or above Tg of the polymer material; and
   expanding the stock tube in the blow mold in order to form a precursor tube;
   wherein the transferring step includes exposing the stock tube, while located within the injection mold, to a cavity within the blow mold.

16. The method of claim 15, wherein the transferring step is performed while the stock tube is at a temperature above Tg of the polymer material.

17. The method of claim 15, wherein the expanding step includes radially expanding the stock tube.

18. The method of claim 17, wherein the expanding step includes axially extending the stock tube.

19. The method of claim 15, further comprising transforming the precursor tube into a stent having a network of stent struts.

20. The method of claim 19, wherein the transforming step includes making a plurality of perforations through a circumferential wall of the precursor tube.

* * * * *

UNITED STATES PATENT AND TRADEMARK OFFICE
CERTIFICATE OF CORRECTION

PATENT NO.        : 8,747,728 B2
APPLICATION NO.   : 13/114941
DATED             : June 10, 2014
INVENTOR(S)       : Wang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 242 days.

Signed and Sealed this
Second Day of August, 2016

Michelle K. Lee
*Director of the United States Patent and Trademark Office*